United States Patent [19]

Winkelmann et al.

[11] 4,211,699

[45] Jul. 8, 1980

[54] ISOCYANATE ADDUCT DIOLS

[75] Inventors: Hans D. Winkelmann; Karlheinz Wolf, both of Cologne; Harald Oertel, Odenthal; Norbert Weimann, Leverkusen, all of Fed. Rep. of Germany

[73] Assignee: Bayer Aktiengesellschaft, Leverkusen, Fed. Rep. of Germany

[21] Appl. No.: 879,740

[22] Filed: Feb. 21, 1978

[30] Foreign Application Priority Data

Feb. 23, 1977 [DE] Fed. Rep. of Germany ....... 2707660

[51] Int. Cl.$^2$ ........................................... C07D 223/10
[52] U.S. Cl. .................. 260/239.3 R; 260/326.5 FL; 260/554; 260/553 A; 260/96.5 R; 260/326.45; 260/326 N; 546/243; 548/171
[58] Field of Search ............... 260/326.3 FL, 239.3 R; 546/243

[56] References Cited

U.S. PATENT DOCUMENTS 3,987,033  10/1976  Ojakaar .................. 260/239.3 R Primary Examiner—Henry R. Jiles
Assistant Examiner—Robert T. Bond
Attorney, Agent, or Firm—Sprung, Felfe, Horn, Lynch & Kramer

[57] ABSTRACT

Isocyanate adduct diols of the formula

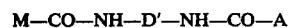

in which M is derived from an amino diol or a hydrazino diol, D' represents the divalent radical of an organic diisocyanate, and A is an isocyanate masking group; and a process for their production.

12 Claims, No Drawings

ISOCYANATE ADDUCT DIOLS

This invention relates to isocyanate adduct diols, to their production and to their use for the production of self-crosslinkable and/or self-crosslinked polyurethanes.

Substantially linear "segmented" polyurethane elastomers have recently acquired considerable significance. They are preferably used in the form of solutions in highly polar solvents and are of particular importance for spinning into polyurethane elastomer filaments, for the coating of textiles, for the production of films and for the manufacture of microporous films or artificial leather products.

The stringent requirements which materials such as these, particularly elastomer filaments, have to satisfy can only be satisfied by suitably selecting corresponding starting materials and reaction parameters. The "segment structure" of these substantially linear polyurethanes performs a considerable function in that, for example, the elasticity is largely determined by the relatively long chain "soft segments" (dihydroxy compounds) whereas the softening point and melting range, resistance to strain at elevated temperatures or in hot water, modulus and strength are largely determined by the so-called "hard segments" of diisocyanate and chain extenders (cf. Chemiker-Zeitung 98, (1974), pages 344–353). The properties of the elastomers are critically determined by the symmetry of the hard segments and by an optimum physical aggregation via hydrogen bonds (H-bond crosslinks) between a plurality of individual hard segments.

This "physical crosslink" through H-bonds may readily be dissolved, for example by highly polar solvents which solvate the hard segment (for example dimethyl formamide), in addition to which the binding force decreases relatively quickly with increasing temperatures.

Accordingly, attempts have repeatedly been made to improve the properties of the elastomers by additional chemical crosslinking, for example by the addition of polyisocyanates, polyethylene imine derivatives, epoxides or polyformaldehyde derivatives, such as polymethylol or polymethylol ether derivatives. In this connection, it was found that subsequent chemical crosslinking of the polyurethanes by the addition of the above compounds can be obtained with insolubilisation and, optionally, in improvement in certain elastic properties, but only at the expense of more important service properties, particularly the thermal and hydrothermal properties. In addition, the temperatures required to initiate crosslinking may be too high or the crosslinking rate too low for practical purposes.

Particularly important service properties are, for example, the behaviour of the filaments under tension or elongation in hot water, for example under dyeing and finishing conditions. They also include the "flow" range of the filaments under predetermined tension on exposure to high temperatures, for example during heat-fixing, and the behaviour of the filaments in elastic knitted fabrics under the conditions of "thermal forming" where high elongations and high temperatures are applied.

This new process technique, in which bra cups for example of knitted polyamide/elasthane fabrics are thermally formed (at around 190° to 195° C.) instead of being machine-stitched, imposes particularly critical conditions on the thermal behaviour of elastomeric filaments.

An object of the present invention is to provide isocyanate adduct diols which are suitable for the production of polyurethane elastomers of the type which
 (a) are chemically crosslinked or are self-crosslinkable,
 (b) contain the crosslinking group in a particular form and hence influence the thermal and hydrothermal properties much more favourably than is the case where conventional crosslinking agents are added,
 (c) have improved thermal formability, and
 (d) show improved resistance to hydrolysis, improved resistance to solvents, improved resistance to thermal degradation and, optionally, reduced surface adhesion.

The crosslinking reactions with the urethane, preferably urea, segments are intended to be readily initiatable by heat, not to require the presence of specific groups (for example tertiary amines) and, in regard to the onset of crosslinking (for example insolubility of the products) to be active with even smaller incorporated quantities than is the case where external crosslinking agents are added.

Other desirable and accomplished improvements will become apparent from the description and the Examples.

The present invention provides isocyanate adduct diols corresponding to the formula:

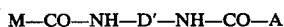

M—CO—NH—D′—NH—CO—A in which
 M is derived from an amino diol or hydrazino diol,
 D′ represents the divalent radical of an organic diisocyanate, and
 A represents an isocyanate masking group.

The isocyanate adduct diols are suitable for the production of solutions of self-crosslinkable polyurethanes obtained by reacting a substantially linear NCO-prepolymer of relatively long chain dihydroxy compounds having a molecular weight of from about 600 to 6000, optionally in the presence of low molecular weight diols, and excess quantities of organic diisocynates and chain extenders in solvents with low molecular weight compounds, such as diols or water, but particularly with N-H-active terminal groups, such as diamines, aminoalcohols, dihydrazide compounds and hydrazine, having molecular weights of from 32 to about 400, by incorporating isocyanate adduct diols corresponding to the formula:

M—CO—NH—D′—NH—CO—A in which
 M is derived from an amino diol or hydrazino diol,
 D′ represents the divalent radical of an organic diisocyanate, and
 A is an isocyanate masking group, into the NCO-prepolymers in quantities of from 0.1 to 10% by weight and preferably in quantities of from 0.25 to 5.0% by weight, based on the solids content.

Accordingly, the present invention also relates to the use of the isocyanate adduct diols for the production of spontaneously crosslinkable and/or crosslinked polyurethanes. For example, solutions of spontaneously crosslinkable polyurethane may be processed into spontaneously crosslinked polyurethane-based shaped articles in the form of filaments, films or coatings.

The distinct improvement in the properties of the shaped articles thus produced may possibly be explained by the fact that, in this case, the crosslinking reaction between two linear segmented polyurethane molecule chains takes place through branching or crosslinking points in different regions of the molecule. Thus, one potential crosslinking point is incorporated as the isocyanate donor diol in controllable form into the actual so-called "soft segment" in the so-called NCO-prepolymer (see formula scheme A), whilst the other crosslinking point arises out of the reaction of the isocyanate donor group with, in general, the "urea hard segment". In this case, therefore, a crosslinking reaction is obtained by preferential reaction with only one hard segment.

During the reaction of the NCO-donor group with urethane groups within the soft segment, which cannot be ruled out as a minor reaction, the only crosslinking reaction which is initiated is a basically particularly desirable crosslinking between soft segments.

However, the known addition of diisocyanates or polyisocyanates or polyisocyanate donors leads to the chemical reaction in two or more different hard segments. Thereafter, both the statistical distribution of the crosslinking points and also the multiple chemical substitution in several hard segments are less favourable. The latter can evidently affect the physical "crosslink" through H-bonds so seriously that, despite the increase in the number of chemical crosslinking bonds, the number of physical crosslinking bonds is overproportionally reduced. This is reflected in the deterioration of a number of properties.

The isocyanate donor diols (a) may be incorporated into the soft segment of the NCO-prepolymers by the methods normally used for the production of prepolymers, for example by using the NCO-donor diols in the reaction of the relatively high molecular weight dihydroxy compounds:

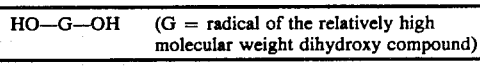

HO—G—OH    (G = radical of the relatively high molecular weight dihydroxy compound)

with excess quantities of diisocyanates

OCN—D—NCO    (D = radical of the diisocyanate)

to form the NCO-prepolymer having the idealised structure according to formula scheme A:

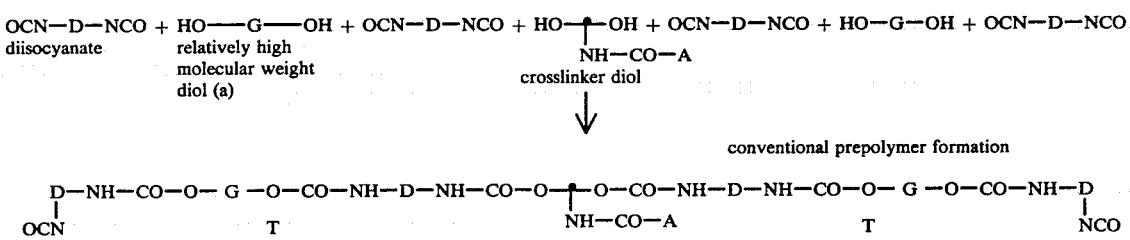

Formula scheme A
NCO-prepolymer formation with incorporation of the monomethylol ether diol I
for example:

Starting materials

OCN—D—NCO + HO——G——OH + OCN—D—NCO + HO—⊤—OH + OCN—D—NCO + HO—G—OH + OCN—D—NCO
diisocyanate    relatively high                        NH—CO—A
                molecular weight                      crosslinker diol
                diol (a)

conventional prepolymer formation

D—NH—CO—O— G —O—CO—NH—D—NH—CO—O—⊤—O—CO—NH—D—NH—CO—O— G —O—CO—NH—D
|                                  |                                  |
OCN              T               NH—CO—A              T              NCO or, as an abbreviation for the modified NCO-prepolymer:    T for abbreviated form

OCN—— T ——⊤—— T ——NCO
         NH—CO—A (b) Chain extension of the NCO-prepolymer with NH-functional chain extenders: H₂N—Y—NH₂ (1:1)

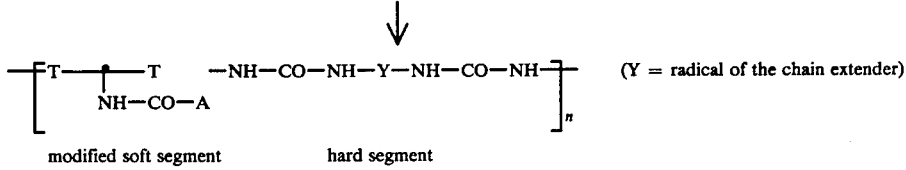

—[T—⊤—T    —NH—CO—NH—Y—NH—CO—NH—]—    (Y = radical of the chain extender)
    |                                            n
    NH—CO—A modified soft segment        hard segment Segmented polyurethane (urea) polymer.

The crosslinkable modified NCO-prepolymer behaves in virtually the same way as an unmodified NCO-prepolymer. The chain extending reaction with diamines, for example, results in the formation of the typical hard segment:

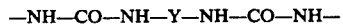

—NH—CO—NH—Y—NH—CO—NH— which, through its interaction via hydrogen bonds with a large number of adjacent hard segments, forms blocks of hard segments physically crosslinked with one another and provides the polymer with its typical elastic properties.

This hard segment is the preferred starting point for the chemical crosslinking reaction with the isocyanate donor group.

Preferred isocyanate adduct diols are those corresponding to the general formula:

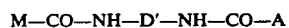

M—CO—NH—D'—NH—CO—A in which M represents the radical

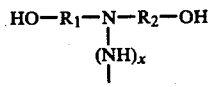

in which $R_1$ and $R_2$ may be the same or different and represent a straight-chain or branched alkylene radical containing up to 12 carbon atoms or a cycloalkylene radical, and x=0 or 1. More particularly, the invention relates to isocyanate adduct diols corresponding to the general formula:

M—CO—NH—D'—NH—CO—A, in which the radical M corresponds to the formula:

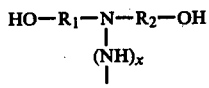

where
$R_1$ represents the radical

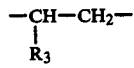

with $R_3$=hydrogen or $C_1$-$C_3$—alkyl, particularly methyl,
$R_2$ represents a straight-chain or branched alkylene radical containing up to 12 carbon atoms or a cycloalkylene radical, and
x=0.

In addition, preferred crosslinkers are those corresponding to the general formula:

M—CO—NH—D'—NH—CO—A, in which the radical M corresponds to the general formula:

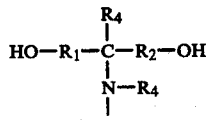

in which $R_1$ and $R_2$ may be the same or different and represent a straight-chain or branched alkylene radical containing up to 12 carbon atoms or a cycloalkylene radical, and $R_4$ represents hydrogen and/or $C_1$-$C_4$—alkyl, particularly methyl.

The isocyanate adduct diols according to the invention consist in principle of the components:

(1) amino diols or hydrazino diols,
(2) organic diisocyanates OCN—D'—NCO, and
(3) "donors" AH.

In principle, the amino diols or hydrazino diols may be any diols which contain another secondary or primary amino group.

One readily accessible group is the alkoxylation products of ammonia or hydrazine:

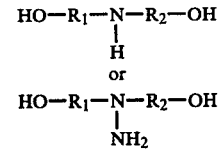

for example
and, preferably, bis-(β-hydroxyethyl)-amine, bis-(β-hydroxypropyl)-amine, (β-hydroxyethyl)-β-hydroxypropylamine, bis-(β-hydroxybutyl)-amine or N,N-bis-(β-hydroxyethyl)-hydrazine, N,N-bis-(α-hydroxypropyl)-hydrazine and N,N-bis-(β-hydroxybutyl)-hydrazine.

Another suitable group are, for example, the monoalkoxylation products of aminoalkanols or aminocycloalkanols, preferably corresponding to the formula:

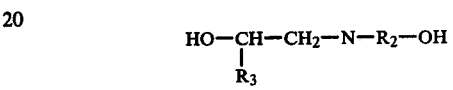

in which $R_2$ and $R_3$ are as defined above
The following are particularly suitable: 4-N-(β-hydroxyethyl)-amino-1-butanol, 6-N-(β-hydroxyethyl)-amino-1-hexanol, 6-N-(β-hydroxypropyl)-amino-1-hexanol, 12-N-(β-hydroxyethyl)-amino-1-dodecanol, 4-N-(β-hydroxyethyl)-amino-1-cyclohexanol, 3-N(β-hydroxyethyl)-amino-1-cyclohexanol, or even other amino derivatives of diols, preferably those corresponding to the formula:

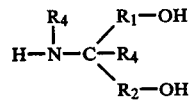

in which
$R_1$, $R_2$ and $R_4$ are as defined above.
The following diols, for example, are preferably used: 2-amino-1,3-propane diol, 2-methylamino-1,3-propane diol, 2-amino-2-methyl-1,3-propane diol, 2-amino-2-ethyl-1,3-propane diol, 3-amino-2,4-pentane diol, 2-amino-1,5-pentane diol or 3-amino-2,5-dimethyl-2,5-hexane diol.

The organic diisocyanates OCN—D'—NCO may be aliphatic or cycloaliphatic dissocyanates, although they are preferably aromatic diisocyanates, for example diphenyl methane-4,4'-diisocyanate, tolylene-2,4-diisocyanate, tolylene-2,6-diisocyanate, phenylene-1,3-diisocyanate, phenylene-1,4-diisocyanate, diphenyl ether-4,4'-diisocyanate and others, but preferably diphenyl methane and tolylene diisocyanates.

Suitable donor compounds A-H are, in principle, any compounds of which the addition products with isocyanates show low thermal stability. Compounds such as these are, for example, phenols, acetoacetic esters, malonic esters, acetyl acetone, phthalimide, benzene sulphonamide, 2-mercaptobenzthiazole or hydrocyanic acid (cf. Kunststoff-Handbuch, Vol. VII, Polyurethane, pages 11 to 14, Carl-Hanser-Verlag, Munich, 1966). One class of compounds which is particularly suitable and preferred for the purposes of the invention is the lactams, for example pyrrolidone, α-piperidone or caprolactam derivatives, for example ε-caprolactam, the methyl caprolactam isomers (for example γ-ethyl caprolactam or γ-tert.-butyl caprolactam). ε-Caprolactam itself is particularly preferred.

The particular suitability of caprolactam was surprising because a relatively high splitting temperature is normally quoted in the literature (cf. High Polymers - Volume XVI - J. H. Saunders, K. C. Frisch, Polyurethanes - Part I - Chemistry, page 120; Interscience Publishers, 1962).

The ready crosslinkability lies in the selected incorporation structure of the diols of the type used in accordance with the invention which provides for a much more favourable crosslinking behaviour than the bis-caprolactam crosslinkers (diisocyanates+2×caprolactam) added in accordance with the prior art.

The novel isocyanate donor diols may be produced by various methods (cf. Production Examples 1, 2, 5).

For example, a bis-adduct may initially be prepared from the diisocyanate and two moles of donor (see, for example, formula I in Production Example 1), and one of the donor groups may subsequently be replaced by reaction with one equivalent of monoamino diol (for example II). In general, the required compound is freed from crystallisation from I or even from the tetrakis-hydroxy derivative (see for example IX).

Another approach is, for example, the process according to Example 5.

In this case, one NCO group is reacted with one equivalent of caprolactam to form the monoadduct isocyanate (VI) which is then reacted with an equivalent quantity of amino diol to form the required product (for example VII or VIII).

Accordingly, the invention also relates to processes for producing the isocyanate adduct diols according to the invention which are distinguished by the fact that an organic diisocyanate and one or two moles of a compound which is capable of forming an addition product of low thermal stability with a diisocyanate are reacted to form a mono- or bis-adduct which is subsequently reacted with a monoamino diol or hydrazino diol.

Relatively high molecular weight dihydroxy compounds which may be used in the synthesis of the polyurethanes are compounds having molecular weights of from about 600 to 6000, preferably from 1000 to 3000, for example polyesters, polyethers, polylactone esters, polyacetals, polycarbonates, mixtures of these groups or co-condensates of these groups, for example polyester ethers, polyester lactone esters, polycarbonate esters and others having melting points preferably below 60° C., more particularly below 50° C., of the type which have been repeatedly described for the synthesis of the segmented polyurethane(urea) elastomers in question.

Examples are adipic acid esters of 1,6-hexane diol, 2,2-dimethyl propane diol, 1,4-butane diol, 1,2-propylene glycol and ethylene glycol or polyesters of mixtures of diols for lowering the melting point of the polyester. Polypropylene glycol ethers, preferably polytetramethylene glycol ethers, give products having a high resistance to hydrolysis. Polycaprolactone (mixed) esters and hexane diol (mixed) polycarbonates and also adipic copolyesters with long-chain diols (for example 1,6-hexane diol) are also particularly preferred by virtue of their increased resistance to hydrolysis.

For improving dyeability, diols containing tertiary amines, such as N-methyl-N,N-bis-(β-hydroxyethylamine) or N-methyl-N,N-bis-(β-hydroxypropylamine), may be used in quantities of from about 0.03 to 0.25 mole/kg during formation of the NCO-prepolymer (cf. German Offenlegungsschrift No. 1,495,830).

The organic diisocyanates used may be known diisocyanates or their structural analogs, although it is preferred to use diphenyl methane-4,4'-diisocyanate, the isomeric tolylene diisocyanates, diphenyl ether-4,4'-diisocyanate and 1,6-hexane diisocyanate, dicyclohexyl methane-4,4-diisocyanate and 3-isocyanatomethyl-3,5,5-trimethyl cyclohexane isocyanate.

The diisocyanates are reacted with the OH-containing compounds in excess quantities, preferably in a molar OH/NCO-ratio of from about 1:1.35 to about 1:3.0, to form the NCO-prepolymer, the NCO-prepolymer preferably containing from about 1.8 to 4.0% of NCO, based on the prepolymer solids.

The NCO-prepolymer may be formed from the components, including the diol component I according to the invention, by methods known in principle either in the melt or preferably in solvents.

For example, all the components may be simultaneously reacted in solvents, such as chlorobenzene, toluene, dioxane or, preferably, in highly polar dimethyl formamide or dimethyl acetamide, at temperatures of from about 20° to about 100° C. to form the prepolymer, or alternatively an NCO-prepolymer may even be initially formed (either wholly or in part) from relatively long chain dihydroxy compounds and the isocyanate adduct diol subsequently reacted to form the final NCO-prepolymer containing the incorporated diol. The type of statistical distribution within the NCO-prepolymer may be influenced according to the procedure adopted.

The isocyanate adduct diols are used in such quantities in the reaction by which the prepolymer is formed that approximately 0.1 to 10% by weight of the diols and preferably 0.25 to 5.0% by weight, based on the prepolymer solids, are incorporated. Since the weight of the chain-extending agent is only of minor importance, substantially the same incorporated quantity, based on the segmented poly(urea)urethane elastomer, may be assumed. A value which effectively characterises the crosslinking density is the number of —N-H—CO—A—groups in mVal/kg because it indicates the equivalents of crosslinker groups incorporated. In the present case, the polyurethane should contain from about 5 to 500 mVal and preferably from about 20 to 200 mVal of crosslinker equivalents (see Examples). Naturally, excessively small quantities may not initiate the effect sufficiently; on the other hand, excessively high quantities of crosslinking groups are also unfavourable because numerous properties (for example elongation at break and modulus) are adversely affected in this way. Accordingly, incorporated quantities of from about 25 to 150 mVal of NCO-donor groups per kg of polyurethane are particularly preferred.

The reaction by which the prepolymer is formed is preferably carried out in dimethyl formamide or dimethyl acetamide as solvent, at temperatures of from about 20° to 60° C. and over periods of from about 20 to 200 minutes.

The NCO-prepolymer formed, modified by incorporation, is then reacted with substantially equivalent quantities of bifunctional N-H-active compounds in highly polar solvents, such as dimethyl formamide, dimethyl acetamide or dimethyl sulphoxide, to form highly viscous solutions of the poly(urea) urethanes by the usual methods of chain extension known per se. In cases where 3-isocyanatomethyl-3,5,5-trimethyl cyclohexane isocyanate is almost exclusively used, it is also possible to use so-called bifunctional "soft solvents", for example toluene/isopropanol mixtures.

The H-reactive chain extenders used are glycols or water, but preferably compounds having molecular weights of from about 32 to about 400, which contain NCO-reactive hydrogen attached to N-atoms and which correspond to the formula $N_2H-Y-NH_2$, where Y = only one bond (→hydrazine),
Y = a difunctional aliphatic, cycloaliphatic, aromatic, araliphatic or heterocyclic radical Z →diamine),
Y = the group

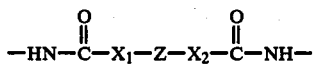

where
Z is as defined above, and
$X_1$ and $X_2$ independently of one another represent a single bond, —O— or —NH— (i.e.→dihydrazides, dicarbazinic esters, disemicarbazides, semicarbazide hydrazide, etc.),
Y = the group

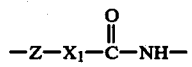

(where Z and $X_1$ are as defined above), i.e.-→aminohydrazides and aminosemicarbazides, or
Y = —NH—CO—NH— (→carbodihydrazide).

Examples of chain extenders corresponding to the formula $H_2N-Y-NH_2$ are as follows: hydrazine or hydrazine hydrate (cf. German Patent No. 1,161,007); primary and/or aliphatic, cycloaliphatic, aromatic or heterocyclic diamines, preferably ethylene diamine or 1,3-diaminocyclohexane; 1,2-propylene diamine and/or m-xylylene diamine (cf. German Pat. No. 1,223,154; U.S. Pat. Nos. 2,929,804 and 2,929,803; German Auslegeschrift No. 1,494,714); amino alcohols, for example aminoethanol or 4-aminocyclohexanol; dihydrazides, for example carbodihydrazide; adipic acid hydrazide (cf. German Pat. Nos. 1,123,467 and 1,157,386); aminocarboxylic acid hydrazides, such as aminoacetic acid hydrazide or β-aminopropionic acid hydrazide (cf. German Auslegeschrift No. 1,301,569); semicarbazide hydrazides such as, for example, α-semicarbazidoacetic acid hydrazide or β-semicarbazidopropionic acid hydrazide (cf. German Pat. No. 1,770,591); or other known NH-compounds of the type described in the above publications and, for example, also in German Offenlegungsschrift No. 2,025,616.

However, particularly preferred chain extenders are ethylene diamine, 1,2-propylene diamine, hydrazine, β-aminopropionic acid hydrazide and β-semicarbazido propionic acid hydrazide, relatively small quantities of so-called "co-extenders" being useable for modifying the properties (for example small quantities of 1,3-diaminocyclohexane or water in addition to ethylene diamine as the main extender).

It is, of course, also possible to use relatively small quantities of monofunctional amino compounds, for example monoamines (diethylamine), monohydrazide derivatives (acethydrizide, picolinic acid hydrazide or butyl semicarbazide) and also asymmetrical dimethyl hydrazine, or very small quantities of trifunctional compounds (for example 1,5,11-triaminoundecane) for increasing functionality (viscosity).

The highly viscous elastomer solutions obtained may be formed by conventional methods, for example by coating onto substrates and evaporating off the solvent to leave highly elastic films and foils, by knife-coating onto textile substrates to form textile coatings, by coagulating solutions (optionally with the addition of a non-solvent) to form microporous films for artificial leather or, preferably and particularly importantly, by spinning the solutions to form elastomeric filaments.

One advantage of the spontaneously crosslinkable polyurethane systems is that, even in the case of wet coagulation and wet spinning processes, there is no danger of the crosslinker being washed out with the solvent or being reduced in its concentration. This is also of particular interest in coagulation processes for artificial leather where a coagulation step in mixtures of dimethyl formamide and water, followed by washing, would result in a loss of additive crosslinkers.

The high stability of the solution containing the self-crosslinkable polyurethanes against undesirable premature crosslinking in solution is particularly favourable. The solutions can be kept ready for processing for weeks without crosslinking. In some cases, the polyurethane mouldings can also be obtained in uncrosslinked form. For example, elastomeric filaments may be spun and processed in uncrosslinked form. It is only at the specific application stage, for example the thermal forming of the knitted fabrics of polyamide/elasthane filaments, that the crosslinking reaction begins at the activation temperature and prevents, for example, the degradation or breaking of the filaments in the knitted fabric.

Depending upon the forming conditions (mainly the forming temperatures), the mouldings obtained are either uncrosslinked (at low temperatures, for example below 100° to 110° C.) or partially or completely crosslinked (at high temperatures and/or with relatively long heating times). In general, the crosslinking reaction will be controlled in accordance with the process and the particular application envisaged.

Heating may be carried out relatively slowly, for example in the case of filaments wound into package form over a period of from 20 to 120 minutes at around 120° to 150° C., or more quickly, for example in the case of coatings over a period of from 1 to 5 minutes at around 130° to 180° C. in drying tunnels or on high-temperature treatment units, such as heating godets or heating grooves where the surface or rather air temperatures can amount for example to between 160° to 250° C. with short contact times of from about 0.5 to 10 seconds. With very short contact times, the temperatures may be even higher (for example by using infrared heating systems).

There is no need to use catalysts for the crosslinking reaction, although catalysts may be present in cases where it is desired to accelerate the crosslinking reaction. Suitable catalysts are in principle any known accelerators for the isocyanate reactions employed in the usual quantities.

EXPLANATION OF THE MEASURING TECHNIQUES AND MEASURING PROCEDURES ADOPTED IN THE EXAMPLES:

Unless otherwise stated, the parts quoted in the Examples represent parts by weight.

The molecular weight of the polyurethane elastomer is characterised by the $(\eta)_i$-value, the so-called inherent viscosity, $$(\eta)_i = \frac{\ln \eta r}{c}$$

where $\eta r$ is the relative viscosity of a solution of the polymer in hexamethyl phosphoramide at 20° C., and c is the concentration in g/100 ml of solution. The measurements were carried out with a c-value of 1.

A high $\eta_i$-value and the insolubility of the mouldings (corresponding to $\eta_i \to \infty$) characterise a high resistance to thermal degradation, as required for heat-fixing and, in particular, for the thermal forming process described above.

The filaments or films were tested for their elastic properties by the measuring techniques described in Belgian Pat. No. 734,194, according to which elongation at break is measured in a tension tester in which the length between the clamps is controlled by a photocell and in which the particular degree of slip through the clamps is compensated.

The elastic values are characterised by measuring the modulus at 300% (in the first elongation curve), the modulus at 150% (in the third recovery curve) and also the permanent elongation (after three times 300% with elongation rates of 400% per minute, 30 seconds after relaxation).

Determination of hot-water extension

A 50 mm long piece of filament is stretched by means of an extending device controlled through a force-measuring head until a contraction stress of 0.25 mN/dtex is applied by the filament. This strain is maintained, optionally by continuously increasing the stretching force, and the degree of extension is determined in air after 25 minutes under load (first value). Thereafter, the stretched filament is immersed in water at 95° C. with the load intact and the total extension occurring is read off after another 25 minutes under load in water (second value). In a third step, the stretched filament is removed from the water, relaxed until it begins to lose tension and the degree of residual elongation is determined (third value). All the measured values are expressed in % of the length between the clamps in accordance with the following scheme:

| 1st value | 2nd value | 3rd value |
| --- | --- | --- |
| Extension in air at 20° C. after 25 minutes under a load of 0.25 $\frac{mN}{dtex}$ [%] | Extension in water at 95° C. after 25 minutes under a load of 0.25 $\frac{mN}{dtex}$ [%] | Residual elongation after complete relaxation in air at 20° C. [%] |

The hydrothermal properties may be rated more highly, the lower the second value (extension in hot water in relation to the first value) and the lower the third value (permanent extension after relaxation).

Determination the reduction in tension in hot water (RTHW) of elastomeric filaments A piece of filament with a length between the groups of 100 mm (biasing weight 0.009 mN/dtex) is stetched by 100% at 20° C. and the filament tension obtained after 2 minutes (mN/dtex) is measured (first value). The filament still stretched by 100% is then immersed in water at 95° C. and the tension obtained after a residence time of 3 minutes is determined (second value). After this measurement, the filament is removed frm the water bath and left standing for 2 minutes at room temperature. Thereafter, the filament still stretched between the clamps is relaxed until free from tension and the degree of residual elongation is measured (third value). Plan of reproduction in the Examples (abbreviation RTHW):

| RTHW | | |
| --- | --- | --- |
| Tension in air at 20° C. (in mN/dtex) | Tension in water at 95° C. (in mN/dtex) | Residual elongation after relaxation (in %) |

The hydrothermal properties may be rated more highly, the higher the second value (tension in hot water in mm/dtex) and the lower the third value (residual elongation after treatment in relaxed form).

Determination of the heat distortion temperature (HDT) of elastomeric filaments The denier of elastomeric filaments is determined after exposure for 3 hours in the absence of tension to standard room conditions (by weighing a piece of filament under an initial load of 0.003 mm/dtex). An elastomeric filament with a length between the clamps of 250 mm is suspended at room temperature in a nitrogen-filled glass tube under an initial load of 0.018 mm/dtex. The tube is surrounded by a heating jacket through which circulates silicone oil heated using a thermostat. The temperature in the tube is initially increased to around 125° C. over a period of about 30 minutes. The temperature is further increased at a rate of 2.1° C. per minute until the elastomeric filament has undergone a change in length of more than 400 mm.

The change in temperature (abscissa value) and extension of the test specimen (ordinate value) are recorded by means of an X-Y-recorder in such an axis ratio that a gradient in the measuring curve of 45° is reached for a relative change in length $\gamma$ of 0.8% per degree of temperature increase.

$$\frac{d}{dT} = 0.8 \frac{percent}{degree} \left(\gamma = \frac{change\ in\ length}{length\ of\ the\ loaded\ specimen\ at\ room\ temperature} \text{ in \%}\right)$$

The heat distortion temperature (HDT) is the temperature which is read off by a vertical projection to the abscissa of the point of contact of the 45° tangent to the temperature/length change curve.

In general, the thermal stability of the elastomers may be rated more highly, the higher the HDT-value measured.

Determination of the hot break time (HBT) of elastomeric filaments

A piece of elastomeric filament is clamped between two clamps (interval 10 cm), stretched by 100% and placed in this form on a 4 cm wide chromium-placed metal plated heated by a thermostat to 193° C. The filament either breaks after a certain residence time or remains stable. After a measuring time of around 3 minutes, the test is terminated if the filament remains intact (characterisation: >180 seconds). The HBT-values are expressed in seconds (sec.) representing the period after which the stretched filaments are seen to break at a temperature of 193° C.

This measurement was developed from a simulation of the behaviour of the filaments in a knitted fabric of polyamide and elasthane filaments. It was found that basically the same results are obtained when a loop of polyamide-6 filament is measured against a loop of elasthane filament (simulation of the stitches) as when the above simplified measuring technique is adopted.

The behaviour of elasthane filaments during thermal forming (extensions per unit area of around 50 to 100%; forming temperatures around 180° to 200° C.) may be correlated relatively well in accordance with the results of the HBT-meausurements.

The following examples are to further illustrate the invention without limiting it.

of the starting material (I, 233 g, m.p. approximately 174° C.) are filtered off.

2.5 parts of water are added to the filtrate and the crystallisate (III) which has accumulated after 24 hours is filtered off under suction. Yield: 104 g (33 % of the theoretical amount), m.p. 151° to 154° C. N calculated: 13.69%, N observed: 13.57%.

The adduct (I) of 2 moles of caprolactam and 1 mole of diphenyl methane-4,4'-diisocyanate is obtained in the form of a highly crystaline substance by reacting 250 g of diisocyanate with 254 g of ε-caprolactam under nitrogen in the melt at 100° C. (strongly exothermic reaction), followed by recrystallisation from boiling toluene. Yield: 372 g, m.p.: 178°-180° C.

The diol adduct (IV) can be correspondingly isolated by reacting 1 mole of bis-caprolactam adduct (I) with 1 mole of N,N-bis-2-hydroxyethyl hydrazine:

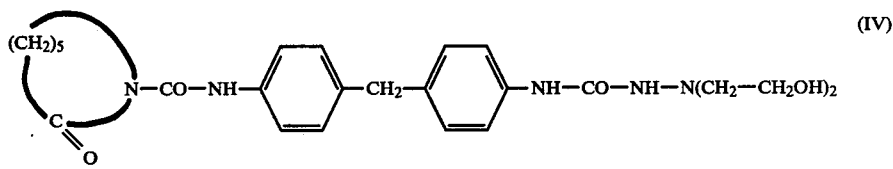

(IV)

EXAMPLE/PRODUCTION SPECIFICATION 1

In accordance with the reaction equation:

EXAMPLE/PRODUCTION SPECIFICATION 2

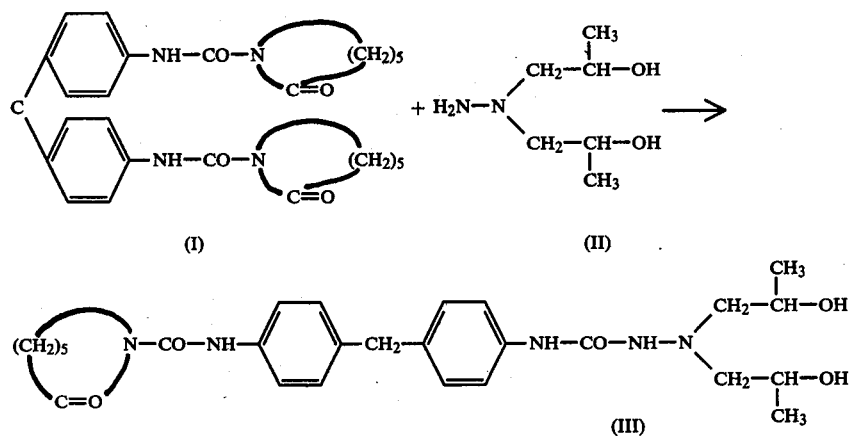

74 g (0.5 mole) of N,N-bis-(2-hydroxypropyl)-hydrazine (II) and 0.5 part of water are introduced at 105° C. into a solution of 476 g (1 mole) of the bis-caprolactam adduct (I) and 2 liters of toluene. The solution is then heated under reflux for 45 minutes, after which another 2.5 liters of toluene are added to it, followed by storage overnight in a refrigerator. The crystallisate formed is filtered off under suction, washed with a little cold toluene and freed in vacuo from the adhering solvent. The crude product (356) is stirred up in 1 liter of methanol at 40° to 45° C., after which the insoluble fractions 238 g (0.50 mole) of the bis-caprolactam adduct (I) are dissolved in 1 liter of boiling toluene and the resulting solution is heated under reflux for 45 minutes with 26 g of diethanolamine (0.25 mole) and 0.25 ml of water.

After cooling, the solvent is distilled off in vacuo, the solid residue is stirred in 1 liter of methanol at 40 ° to 45° C. and the residue (bis-adduct-I) is isolated by filtration. The methanolic solution is precipitated in 1500 ml of water.

The residue is suspended in and digested with ether. The residual solid (V), m.p. 135°-143° C., is recrystallised from chlorobenzene→m.p. 146°-148° C.

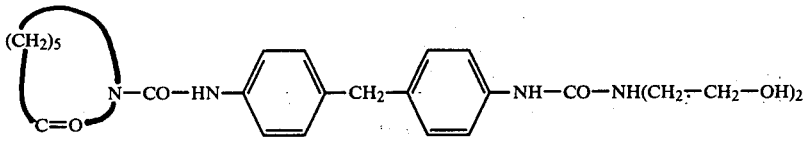

(V)

N calculated: 11.95%   O calculated: 17.1%
N observed: 11.82%    O observed: 17.4%.

EXAMPLE 3

500 parts of a 1,6-hexane diol/2,2-dimethyl-1,3-propane diol/adipic acid polyester (molar ratio of the diols 65:35) having a molecular weight of 1875, 10.68 parts of N-methyl-bis-(β-hydroxypropyl)-amine, 37.2 parts of the diol-NCO-adduct (III) (corresponding to 100 mVal of NCO/caprolactam crosslinker groups per kg of elastomer), 163.3 parts of diphenyl methane-4,4′-diisocyanate and 178 parts of dimethyl formamide are reacted to 1 hour at 50° C. to form the NCO-prepolymer (2.79 % of NCO in the solid substance).

6.85 parts of ethylene diamine are dissolved in 1230 parts of dimethyl formamide and converted with 10 parts of dry ice into the carbamate suspension. 400 parts of the prepolymer solution are added with intensive stirring to the carbamate suspension, resulting in the formation of an elastomer solution with a viscosity of 250 poises. 6 ml of a solution of 6.70 parts of hexane diisocyanate in 50 parts of dimethyl formamide are added dropwise to the elastomer solution thus formed, resulting in the formation of a viscous homogeneous elastomer solution having a viscosity of 445 poises. The elastomer solution is spun by the dry spinning process.

Portions of the solution are diluted to 16% and are wet spun and cast to form films. The films can still be smoothly dissolved after a drying time of 30 minutes at 70° C. plus 30 minutes at 100° C. After heating for 30 minutes to 130° C., the film is insoluble in dimethyl formamide, even on heating to 80° C.

The film has a strength of 0.64 cN/dtex, an elongation of 597%, a modulus at 300% elongation of 0.11 cN/dtex and a heat distortion temperature (HDT) of 190° C.

Like the film, the wet-spun filaments can be subsequently crosslinked by heating (for example for 30 minutes to 130° C.), after which they are insoluble in DMF.

Testing of dry-spun elastomer filaments which have been aftertreated for 1 hour at 130° C. on bobbins shows that the filaments have become insoluble and have a hotbreak time of >180 seconds at 193.7° C. and 100% elongation (the measurements are normally terminated after 180 seconds). Further testing failed to show any breaks even after 420 seconds. By contrast, elastomer filaments with the same composition, but without any crosslinking agent incorporated in them, break after only about 15 to 30 seconds.

Accordingly, the advantages of the crosslinking process according to the invention lie both in the insolubilisation obtained and, more particularly, in the considerably improved hot break time.

EXAMPLE 4

400 parts of the polyester described in Example 3 (molecular weight 1875), 8.29 parts of N-methyl-bis-(β-hydroxypropyl)-amine, 28.8 parts of the diol-NCO-adduct (III) (corresponding to approximately 100 mVal of NCO -/Cl-crosslinker groups per kg of elastomer substace), 116.7 parts of diphenyl methane-4,4′-diisocyanate and 138 parts of dimethyl formamide (DMF) are converted into prepolymer after 85 minutes at 40° to 43° C. (2.11% of NCO, based on solids - i.e. the prepolymer contains fewwer NCO-groups than in Example 1 and, hence, also less "hard segment" in the polyurethane).

5.48 parts of ethylene diamine in 1070 parts of dimethyl formamide are converted with 10 g of $CO_2$ into the carbamate ($H_3N^{\oplus}-CH_2-CH_2-COO^{\ominus}$), reacted while stirring with 450 parts of the NCO-prepolymer and diluted with 305 parts of dimethyl formamide to c=20%/242 poises. By adding 1.14 parts of hexane diisocyanate in 10 parts of dimethyl formamide, the viscosity of the solution increases to 415 poises. The solution is dry spun (see below), wet spun and converted into films by drying (for 70 mins. at 100° C.).

COMPARISON EXAMPLE

An NCO-prepolymer is prepared in the same way as described in Example 4, but without the incorporation of the diol-crosslinker-adduct III (NCO-content 2.10 % NCO), and the chain-extending reaction is carried out with ethylene diamine. An elastomer solution having a viscosity of 661 poises (22 % solution) is obtained.

If the films are cast and dried for 70 mins. at 100° C., the films from both solutions are still soluble in DMF. After heating for 30 minutes at 130° C., the film of the self-crosslinkable elastomer solution according to Example 4 has become insoluble in DMF. The film according to comparison tests remain soluble.

If the solutions are wet spun in 90/10 mixtures of water/DMF heated to 80° C. and the filaments thus obtained are subsequently dried for 20 minutes at 130° C., it is again only the self-crosslinkable substance according to the invention which has become substantially insoluble, the properties of the filaments being considerably improved as a result of crosslinking, particularly in their thermal properties (for example the heat distortion temperature (HDT) and the hot break time at 193.7° C./100% elongation):

|  | Tensile strength cN/dtex | Elongation % | Permanent elongation % | HDT °C. | HBT (sec. at 193.7° C./ 100% elongation) |
|---|---|---|---|---|---|
| According to the invention (Example 4) | 0.64 | 562 | 16 | 181 | ≧180 |
| Comparison test | 0.59 | 565 | 19 | 176 | 14.9 |

If, instead of III, the diol-crosslinker adduct IV is used in an equivalent quantity in Example 4, the same crosslinking and, hence, improvement in properties is obtained.

EXAMPLE 4b 200 parts of a polyester corresponding to Example 3 (molecular weight 1950), 12.48 parts of the monoadduct diol IV (100 mVal of crosslinker per kg of elastomer), 49.26 parts of diphenyl methane-4,4'-diisocyanate and 66 parts of dimethyl formamide are reacted to 180 minutes at 42° C. to form the NCO-preadduct (2.21% of NCO in the solid substance).

For the chain-extending reaction, 107.5 parts of the above NCO-prepolymer solution are stirred into a suspension of 1.36 parts of ethylene diamine in 224 parts of dimethyl formamide and 3 parts of dry ice. A clear, homogeneous elastomer solution having a viscosity of 346 poises is formed.

Films of this solution (dried for 70 minutes at 100° C.) are soluble in dimethyl formamide. After heating (for 30 minutes at 130° C.), the films are insoluble in dimethyl formamide and have a hot break time (HBT) at 193.7° C./100% elongation of 208 seconds. (By contrast, crosslinker-free films show hot break times of only about 15 seconds and remain soluble; after heating at 130° C., they even show a reduction in molecular weight of around 10%).

If the crosslinker-containing but still soluble films (dried for 70 minutes at 100° C.) are measured for their hot break time, they crosslink during the measurement are dissolved at 50° C. and heated for 65 minutes to 60° C. The solution separates increasingly into two phases which are separated in a separation funnel. The lower phase is washed three times with 50 ml of petroleum ether, after which its NCO-content is titrimetrically determined.

300 ml of acetone are added to this layer which contains the CL-monoadduct isocyanate (VI), after which a quantity of diethanolamine equivalent to the NCO-content (based on the secondary amino group) is added dropwise while stirring and cooling with ice (internal temperature kept below 20° C. by cooling). The solution is then poured into 1 liter of water with precipitation of VII, the supernatant liquid is decanted off and the greasy deposit is dried in vacuo at 40° to 50° C. 144 parts of a white, powdery product VII, m.p. 130° C. (sint. 105°-110° C.) are isolated.

| Analysis (VII): | calculated: | observed: |
|---|---|---|
| C. | 58.3 | 58.8% |
| N | 14.3 | 14.3% |
| H | 7.2 | 7.2% |
| O | 20.0 | 19.8% |

If, instead of diethanolamine, an equivalent quantity of 2-amino-2-methyl-1,3-propane diol is used in the reaction with the CL-monoadduct isocyanate VI, the product VIII is obtained (m.p. 132° to 138° C.).

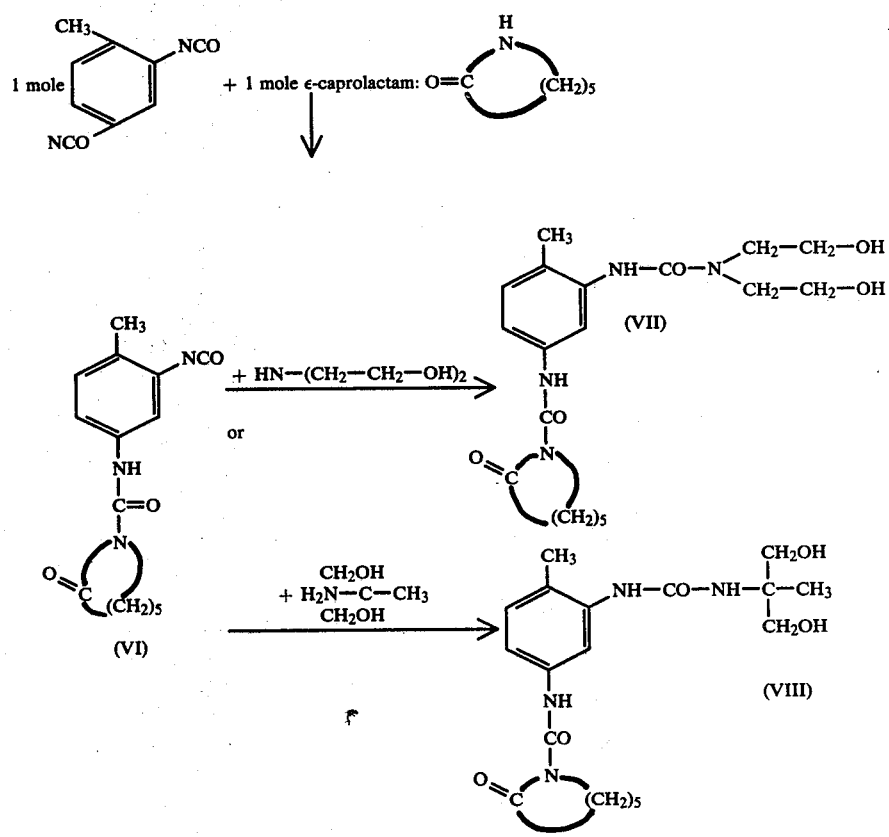

and give a heat distortion temperature (HDT) of 185° C. which is high for their relatively low NCO-content.

EXAMPLE/Production Specification (5)

113 parts of ε-caprolactam (CL), 174 parts of tolylene-2,4-diisocyanate and 420 parts of petroleum ether The tetra-kis-hydroxy urea IX expected as a secondary product was produced from 1 mole of tolylene-2,4-diisocyanate and 2 moles of diethanolamine in dimethyl formamide solution at 0° to 5° C. and precipitated by the addition of a large quantity of acetone (m.p. 143° C., white powder).

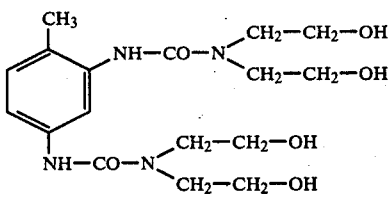

The same reaction of tolylene diisocyanate with 2-amino-2-methyl-1,3-propane diol also gives the tetra-kis-hydroxy urea, m.p. 197° to 200° C.

To produce the bis-caprolactam adduct (X) of tolylene diisocyanate, a mixture of equivalent quantities of the starting materials is heated to 90° C., after which exothermic heating to about 140° C. occurs. The product is heated for another 2 hours to 90° C. The product is recrystallised from 2 liters of toluene, m.p. 170°-173° C.

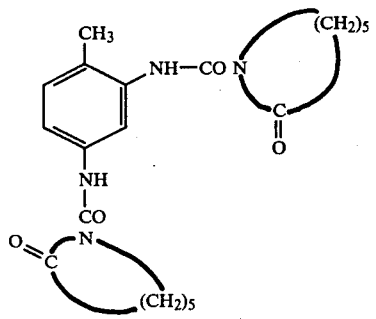

EXAMPLE 6

500 parts of an adipic acid/1,6-hexane diol/2,2-dimethyl-1,3-propane diol polyester (molecular weight 1950), 27.82 parts of the monoadduct diol VII (100 mVal of crosslinker groups per kg of polyurethane), 10.43 parts of bis-($\beta$-hydroxypropyl)-methylamine, 177.5 parts of diphenyl methane-4,4'-diisocyanate and 174 parts of dimethyl formamide are reacted for 80 minutes at 40° C. to form the NCO-prepolymer (2.82% of NCO in the solid substance).

420 parts of the NCO-prepolymer are introduced with intensive stirring into a suspension of 6.90 parts of ethylene diamine in 1080 parts of dimethyl formamide and 10 parts of dry ice, resulting in the formation of a clear, homogeneous and highly viscous elastomer solution (520 poises).

Comparison Example (a)—no crosslinker incorporated—no addition

An elastomer solution is prepared in the same way from the same starting materials, but without the incorporation of the crosslinker diol VII. The corresponding NCO-preadduct has an NCO-content (in the solid substance) of 2.80%. The chain-extended polyurethane solution has a viscosity of 640 poises/22% (or 328 poises/20%).

Comparison Example (b)—without incorporation of crosslinker, but with addition of 100 mVal of bis-crosslinker X per kg of polyurethane.

250 parts of the 22% crosslinker-free elastomer solution according to Comparison Example (a) are stirred with 1.15 parts of the bis-caprolactam adduct X ("bis-crosslinker") and 25 parts of dimethyl formamide (320 poises).

Comparison Example (c)—without incorporation of crosslinker, but with addition of 200 mVal of X/kg of polyurethane.

250 parts of the elastomer solution a are stirred with 2.3 parts of X and 30 parts of dimethyl formamide (306 poises).

Comparison Example (d)

If an attempt is made to incorporate an NCO-prepolymer corresponding to the Example, but with the incorporation of an equivalent quantity of the tetra-kis-hydroxy urea IX (instead of the monoadduct-crosslinker diol VII), complete crosslinking of the prepolymer occurs during the actual formation of the prepolymer.

Approximately 0.12 mm thick films are cast from the solutions of the Example according to the invention and Comparison Examples a and c and dried (for 45 minutes at 70° C.+45 minutes at 100° C.). All the films were soluble in cold dimethyl formamide.

The films are additionally heated to 30, 60, 120 and 180 minutes at 130° C.

The film according to comparison test (a) remains soluble (no possibility of crosslinking).

The films according to comparison tests (b) and (c) remain soluble, i.e. uncrosslinked, after 30, 60 and 120 minutes at 130° C. and are only slightly crosslinked after 3 hours at 130° C. (substantially soluble in cold DMF). Even after 1 hour at 150° C., films (b) and (c) are uncrosslinked so that they remain soluble in dimethyl formamide heated to 95° C. (they only undergo pronounced swelling in cold DMF). By contrast, the film according to the invention is crosslinked after only 30 minutes at 130° C. and is still insoluble in dimethyl formamide, even after 20 minutes at 95° C.

The Example demonstrates the advantage of the self-crosslinkable structure incorporated compared with the "bis-caprolactam donors" or rather "crosslinkers" known per se.

If the solutions are wet spun through 20-bore spinnerets 0.12 mm in diameter into a coagulation bath heated to 80° C. of water and dimethyl formamide (90/10), and if the filaments thus formed are wound into package form at a speed of about 5 meters per minute, followed by treatment in a water bath at 50° C. and then at 90° C. to remove the solvent, drying in air and tempering for 1 hour at 130° C., the following results are obtained:

| | Denier (dtex) | Strength (cN/dtex) | Elongation (%) | Modulus/300% (cN/dtex) | Hot break time at 193.7° C./100% (seconds) | Solubility in DMF at 20° C. |
|---|---|---|---|---|---|---|
| According to the invention (100 mVal/kg of incorporated crosslinker) | 309 | 0.65 | 606 | 187 | 96 | insoluble |

-continued

| | | | | | | |
|---|---|---|---|---|---|---|
| a) Comparison without cross-linker | 304 | 0.52 | 530 | 159 | 30 | soluble |
| b) Comparison with 100 mVal/kg of bis-crosslinker (additive) | 294 | 0.52 | 540 | 159 | 14 | soluble |
| c) Comparison with 200 mVal/kg of bis-crosslinker (additive) | 317 | 0.47 | 537 | 144 | 12.8 | soluble, dissolving somewhat slowly |

Whereas the filaments according to the invention containing 100 mVal/kg of incorporated crosslinker groups are highly crosslinked (insoluble) and show a considerable improvement in their hot break time, the additively introduced "bis-crosslinker" does not have a crosslinking effect so that the hot break times show no improvement. Tempering times of 1 hour at 150° C. are required for initiating a certain crosslinking effect in the case of (b) and (c), although this adversely affects the other properties and, in practice, is too slow for a continuous crosslinking reaction.

If the solutions are dry spun (solution according to the invention) for comparison with the crosslinker-free solution according to comparison Example (a), the elastomer filaments obtained also differ considerably in their thermal stability. The hot break time of the uncrosslinked filaments is increased from 31 seconds (at 193.7° C./100% elongation) to 96.5 seconds in the case of the filament crosslinked in accordance with the invention, in addition to which the stability of the filament tension in hot water is improved.

EXAMPLE 7

(a) NCO-Preadduct 500 parts of an adipic acid/1,6-hexane diol/2,2-dimethyl-1,3-propane diol polyester (molar ratio of the glycols 65/35) having a molecular weight of 1950, 27.82 parts of the monoadduct diol (VII), 10.43 parts of bis-($\beta$-hydroxypropyl)-methylamine, 157.5 parts of diphenyl methane-4,4'-diisocyanate and 174 parts of dimethyl formamide are reacted for 95 minutes at 40° C. to form an NCO-prepolymer (NCO-content 2.82% in the solid substance).

(b) Chain extension with hydrazine hydrate 5 parts of the NCO-preadduct (a) are added with intensive stirring at 2.89 parts of hydrazine hydrate in 537 parts of dimethyl formamide. A clear highly viscous elastomer solution is formed (378 poises/22%).

The solution is cast into films and dried (for 45 minutes at 70° C. +45 minutes at 100° C.). The highly elastic films formed (tensile strength 0.64 cN/dtex; elongation at break 586%) are still soluble in dimethyl formamide. If the films are heated for 30 minutes at 130° C., they crosslink and become insoluble in dimethyl formamide (20 minutes at 95° C.).

After brief drying in a hot air duct at about 150° C., elastomer filaments wet spun in the usual way show an excellent hot break time of 100 seconds at 193.7° C./100% elongation by virtue of their crosslinking.

(c) Reaction with $\beta$-semicarbazidopropionic acid hydrazide 9.30 parts of $H_2N.NH.CO.NH.CH_2CH_2.CO.NH.NH_2$ are dissolved in 18 parts of hot water, diluted with 542 parts of dimethyl formamide are reacted over a period of 5 minutes to form the elastomer solution (420 poises) by the introduction of 210 parts of the NCO-preadduct solution (a).

Portions of the solution are cast into films and dried (for 70 minutes at 100° C.) to form highly elastic films (tensile strength 0.60 cN/dtex; elongation 590%). The films are still uncrosslinked (soluble in dimethyl formamide at room temperature). If the films are heated for 30 minutes to 130° C., they are crosslinked and become insoluble in dimethyl formamide (test temperature 95° C./20 minutes).

Portions of the solution are wet spun into filaments (coagulation in mixtures of water and DMF (80/20) at 80° C.). For complete solvent extraction, the filaments are aftertreated for 1 hour in water at 90° C. and dried in air. The filaments are still readily soluble in dimethyl formamide. The hot break time of these filaments, which is important for their thermal forming is only 1 second at 193.7° C./100% elongation and is therefore inadequate. If the elastomer filaments are thermally aftertreated, for example for 1 hour at 130° C. or by passage in the form of 10 loops over a heating godet heated to 175° C. at a speed of 100 meters per minute, the hot break time undergoes a considerable increase to 17.5 seconds.

The filaments show good elastic properties: tensile strength 0.72 cN/dtex at 542 % elongation; modulus at 300 % elongation: 0.29 cN/dtex; hot water elongation (HWE): 20/89/26 %; reduction in hot water (RTHW): 0.68 mN/dtex/0.24 mN/dtex/36 %.

EXAMPLE 8

200 parts of an adipic acid/1,6-hexane diol/2,2-dimethyl-1,3-propane diol (65/35) polyester (molecular weight 1900), 4.09 parts of N,N-bis-($\beta$-hydroxypropyl)-methylamine, 10.90 parts of the monoadduct diol VIII, 58.7 parts of diphenyl methane-4,4'-diisocyanate and 68.5 parts of dimethyl formamide are reacted for 95 minutes at 40° C. to form a prepolymer having an NCO-content of 1.80.

A suspension of 1.24 parts of ethylene diamine, 306 parts of dimethyl formamide and 2 parts of dry ice is reacted with 100 parts of the above NCO-prepolymer solution to form an elastomer solution.

The solution is cast and dried to form films which, after 30 minutes at 130° C., are insoluble in dimethyl formamide both at room temperature and at 95° C.

EXAMPLE 9

300 parts of a polytetramethylene ether diol (molecular weight 2000), 6.15 parts of N,N-bis-($\beta$-hydroxypropyl)methylamine, 88.41 parts of diphenyl methane-4,4'-diisocyanate and 16.39 parts of the monoadduct diol VII (approxiately 100 mVal of NCO-donor per kg of elastomer solids) are reacted with 103 parts of dimethyl formamide for 50 minutes at 40° C. and then for 90 minutes at room temperature to form an NCO-prepolymer (NCO-content 2.36 % in the solid substance).

3 Parts of dry ice and then 107.5 parts of the above NCO-prepolymer solution are added to 1.45 parts of ethylene dimanine in 270 parts of dimethyl formamide. A homogeneous solution having a viscosity of 234 poises is formed.

Portions of the solution are cast and dried (for 70 minutes at 100° C.) to form films. Films heated for 30 minutes at 130° C. remain undissolved in cold dimethyl formamide. Maximum crosslinking is obtained after 60 minutes at 130° C. (or after 30 minutes at 150° C.), the film remaining stable, i.e. undissolved and structurally intact, in dimethyl formamide at 95° C., even after 3 hours. The tensile strength of the films is 0.68 cN/dtex, their elongation is 684% and their modulus at 300% is 0.115 cN/dtex.

Another portion of the solution is spun into a bath of water and DMF (80/20) heated to 80° C., run off at 10 meters per minute and subsequently freed from the solvent in hot water (90° C.). The filaments are still soluble in dimethyl formamide. Their tensile strength is 0.64 cN/dtex for 644% elongation and their modulus at 300% elongation is 0.15 cN/dtex.

When tested for their thermal behaviour at 193.7° C./100% elongation (measurement of the hot break time/HBT), the filaments break after 10.2 seconds. Although this is better than in the comparison test without the crosslinker diol incorporated (2 seconds), it is still not entirely satisfactory. However, if the filaments are afterheated for 1 hour at 130° C. or if they are passed over heating godets having a surface temperature of 180° C., the filaments become insoluble in DMF and the hot break time increases considerably to 36.3 seconds at 193.7° C. This is sufficient for thermal forming.

When the filaments are tested (without thermal aftertreatment) for their heat distortion temperature (HDT), a very high HDT-value of 193.5° C. is observed. The filaments are crosslinked during the relatively slow measurement which explains why they reached this high value. Similar crosslinking occurs during the usual treatment of elastic knitted fabrics on a tentering frame (for example for 20 to 30 seconds at 180° to 195° C.).

Comparison Test

A polyurethane is synthesized in the same way as before, but in the absence of the monoadduct diol VII (and in the absence of its equivalent quantity of diphenyl methane-4,4'-diisocyanate). Films of this solution are not crosslinkable. Wet-spun filaments show a considerably reduced hot break time (≦2 seconds) and remain soluble.

What is claimed is:

1. An isocyanate adduct diol corresponding to the formula

in which
M corresponds to the formula

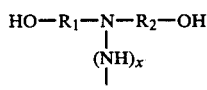

where
R$_1$ and R$_2$ may be the same or different and represent a straight chain or branched alkylene radical with up to 12 carbon atoms or a cyclohexylene radical, and x=0 or 1 or M corresponds to the formula

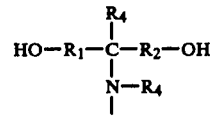

in which
R$_1$ and R$_2$ are the same or different and each represents a straight chain or branched alkylene radical with up to 12 carbon atoms or a cyclohexylene radical, and R$_4$ represents hydrogen and/or C$_1$-C$_4$ alkyl D' represents a divalent radical derived from diphenyl methane-4,4'-diisocyanate, tolylene-2,4-diisocyanate, tolylene-2,6-diisocyanate, phenylene-1,3-diisocyanate, phenylene-1,4-diisocyanate or diphenyl ether-4,4'-diisocyanate and A is an isocyanate masking group derived from pyrrolidone, α-piperidone, ε-caprolactam, methyl caprolactam, γ-ethyl caprolactam or γ-tert.-butyl caprolactam.

2. The isocyanate adduct diol as claimed in claim 1, in which M corresponds to the formula:

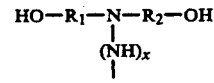

where
R$_1$ and R$_2$ may be the same or different and represent a straight-chain or branched alkylene radical with up to 12 carbon atoms or a cycloalkylene radical, and x=0 or 1.

3. The isocyanate adduct diol as claimed in claim 2 in which
R$_1$ represents the radical

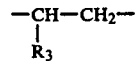

with R$_3$=hydrogen or C$_1$—C$_4$—alkyl,

R$_2$ represents a straight-chain or branched alkylene radical with up to 12 carbon atoms or a cyclohexylene radical, and x=0.

4. The isocyanate adduct diol as claimed in claim 3, wherein R$_3$ is methyl.

5. The isocyanate adduct diol as claimed in claim 1, in which M corresponds to the general formula:

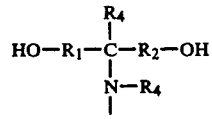

in which
R₁ and R₂ are the same or different and each represents a straight-chain or branched alkylene radical with up to 12 carbon atoms or a cycloalkylene radical, and
R₄ represents hydrogen and/or C₁—C₄—alkyl.

6. The isocyanate adduct diol as claimed in claim 5, wherein R₄ is methyl.

7. A process for producing an isocyanate adduct diol as defined in claim 1 which comprises reacting an organic diisocyanate selected from the group consisting of diphenyl methane-4,4'-diisocyanate, tolylene-2,4-diisocyanate, tolylene-2,6-diisocyanate, phenylene-1,3-diisocyanate, phenylene-1,4-diisocyanate and diphenyl ether-4,4'-diisocyanate with two mols of a compound selected from the group consisting of pyrrolidone, α-piperidone, ε-caprolactam, methyl caprolactam, γ-ethyl caprolactam and γ-tert.-butyl caprolactam to form a bis-adduct, and reacting said bis-adduct with one equivalent of a compound of the formula

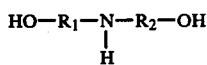

or a compound of the formula

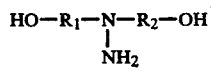

wherein, in each formula,
R₁ and R₂ can be the same or different and represent straight or branched alkylene radicals having up to 12 carbon atoms or a cyclohexylene radical.

8. A process for the production of an isocyanate adduct diol as defined in claim 1 which comprises reacting an organic diisocyanate selected from the group consisting of diphenyl methane-4,4'-diisocyanate, tolylene-2,4-diisocyanate, tolylene-2,6-diisocyanate, phenylene-1,3-diisocyanate, phenylene-1,4-diisocyanate, and diphenyl ether-4,4'-diisocyanate with one equivalent of a compound selected from the group consisting of pyrollidone, α-piperidone, ε-caprolactam, methyl caprolactam, γ-ethyl carpolactam and γ-tert.-butyl caprolactam to form an adduct and reacting the adduct thus formed with one equivalent of a compound of the formula

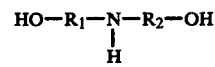

or a compound of the formula

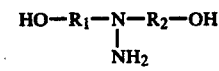

wherein, in each formula,
R₁ and R₂ are the same or different and represent straight chain or branched alkylene radicals having up to 12 carbon atoms or a cyclohexylene radical.

9. The process as claimed in claim 7, wherein the adduct is reacted with a compound of the formula

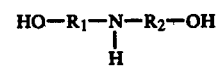

in which R₁ represents the radical

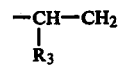

with
R₃=hydrogen or C₁—C₄—alkyl, and
R₂ represents a straight-chain or branched alkylene radical containing up to 12 carbon atoms or a cycloalkylene radical.

10. The process as claimed in claim 8, wherein the adduct is reacted with a compound of the formula

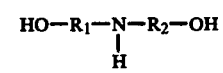

in which R₁ represents the radical

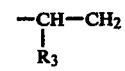

with
R₃=hydrogen or C₁—C₄—alkyl, and
R₂ represents a straight-chain or branched alkylene radical containing up to 12 carbon atoms or a cycloalkylene radical.

11. The process as claimed in claim 9, wherein R₃ represents methyl.

12. The process as claimed in claim 10, wherein R₃ represents methyl.

* * * * *

UNITED STATES PATENT AND TRADEMARK OFFICE
CERTIFICATE OF CORRECTION

PATENT NO. : 4,211,699            Page 1 of 2

DATED : July 8, 1980

INVENTOR(S) : Hans D. Winkelmann, Karlheinz Wolf, Harald Oertel and Norbert Weimann It is certified that error appears in the above—identified patent and that said Letters Patent is hereby corrected as shown below:

| Column | Line | |
|---|---|---|
| 11 | 61 | insert "of" after "Determination". |
| 11 | 64 | "stetched" should be --stretched--. |
| 12 | 2 | "frm" should be --from--. |
| 13 | 7 | "6filament" should be --6 filament--. |
| 13 | 40 (diagram I) | "C$\diagup_{\diagdown}$" should be --$\underset{\diagdown}{\overset{\diagup}{CH_2}}$--. |

UNITED STATES PATENT AND TRADEMARK OFFICE
CERTIFICATE OF CORRECTION

PATENT NO. : 4,211,699

DATED : July 8, 1980

INVENTOR(S) : HANS D. WINKELMANN, KARLHEINZ WOLF, HARALD OERTEL, and NORBERT WEIMANN It is certified that error appears in the above—identified patent and that said Letters Patent is hereby corrected as shown below:

| Column | Line | |
|--------|------|---|
| 14 | 10 | "crystaline" should be --crystalline--. |
| 16 | 13 | "substace" should be --substance--. |
| 16 | 17 | "fewwer" should be --fewer--. |
| 20 | 16 | insert ")" after "a". |
| 20 | 30 | "a and c" should be --a) to c)--. |
| 23 | 5 | "dimanine" should be --diamine--. |

Signed and Sealed this

Twenty-first Day of October 1980

[SEAL]

Attest:

SIDNEY A. DIAMOND

Attesting Officer

Commissioner of Patents and Trademark